US007918797B2

(12) United States Patent
Bae et al.

(10) Patent No.: US 7,918,797 B2
(45) Date of Patent: Apr. 5, 2011

(54) ULTRASOUND DIAGNOSTIC SYSTEM AND METHOD FOR FORMING MULTIPLE RECEIVING SCAN LINES

(75) Inventors: Moo Ho Bae, Seoul (KR); Ronald E. Daigle, Redmond, WA (US); Chi Young Ahn, Seoul (KR); Ra Young Yoon, Seoul (KR)

(73) Assignee: Medison Co., Ltd., Hongchun-gun (KR)

( * ) Notice: Subject to any disclaimer, the term of this patent is extended or adjusted under 35 U.S.C. 154(b) by 598 days.

(21) Appl. No.: 11/752,045

(22) Filed: May 22, 2007

(65) Prior Publication Data

US 2008/0009725 A1 Jan. 10, 2008

(30) Foreign Application Priority Data

May 23, 2006 (KR) .................. 10-2006-0046253
Nov. 17, 2006 (KR) .................. 10-2006-0114072

(51) Int. Cl.
*A61B 8/00* (2006.01)
(52) U.S. Cl. ..................... 600/447; 600/437
(58) Field of Classification Search .............. 600/447
See application file for complete search history.

(56) References Cited

U.S. PATENT DOCUMENTS

| 5,469,851 | A | * | 11/1995 | Lipschutz | 600/447 |
| 6,042,547 | A | * | 3/2000 | Wright et al. | 600/447 |
| 6,695,783 | B2 | * | 2/2004 | Henderson et al. | 600/443 |
| 2001/0051772 | A1 | | 12/2001 | Bae | |
| 2002/0082500 | A1 | | 6/2002 | Henderson et al. | |
| 2006/0058656 | A1 | | 3/2006 | Kristoffersen et al. | |
| 2007/0016066 | A1 | | 1/2007 | Bae et al. | |

FOREIGN PATENT DOCUMENTS

| JP | 2004-194981 | 7/2004 |
| JP | 2004-216047 | 8/2004 |
| WO | WO 2004/064619 A2 | 8/2004 |
| WO | WO 2006/042067 A2 | 4/2006 |

OTHER PUBLICATIONS

Karthik Ranganathan, et al., "A Prototype Low Cost Handheld Ultrasound Imaging System", Proceedings of the SPIE—The International Society for Optical Engineering, XP-002447113, vol. 5373, No. 1, 2004, pp. 24-32.

* cited by examiner

*Primary Examiner* — Eric F Winakur
*Assistant Examiner* — Hien Nguyen
(74) *Attorney, Agent, or Firm* — Oblon, Spivak, McClelland, Maier & Neustadt, L.L.P.

(57) ABSTRACT

Embodiments of the present invention may provide an ultrasound imaging system and method for forming multiple receiving scan lines from one original receiving scan line. Ultrasound signals reflected from one original receiving scan line are converted into analog signals having a center frequency. The analog signals are converted into digital data. The digital data are coarsely delayed, wherein the coarsely delayed data are extracted at a rate of n-times of the center frequency. Data of the multiple receiving scan lines are formed by performing fine delay and interpolation. For the interpolation, parts of the extracted data are selected at a rate of n-times of the center frequency and the multiple receiving scan lines.

8 Claims, 7 Drawing Sheets

ULTRASOUND DIAGNOSTIC SYSTEM AND METHOD FOR FORMING MULTIPLE RECEIVING SCAN LINES

The present application claims priority from Korean Patent Applications Nos. 10-2006-0046253 and 10-2006-0114072 filed on May 23, 2006 and Nov. 17, 2006, respectively, the entire subject matters of which are incorporated herein by reference.

BACKGROUND

1. Field

The present invention generally relates to ultrasound diagnostic systems, and more particularly to an ultrasound diagnostic system and a method for forming multiple receiving scan lines.

2. Background

An ultrasound diagnostic system has become an important and popular diagnostic tool since it has a wide range of applications. Specifically, due to its non-invasive and non-destructive nature, the ultrasound diagnostic system has been extensively used in the medical profession. The ultrasound is transmitted to a target object through a probe equipped in the ultrasound diagnostic system. Ultrasound echoes from the target object reach the probe. The ultrasound echoes are converted into electrical receiving signals in analog-form. Ultrasound images are formed based on the electrical receiving signals obtained from the ultrasound echoes.

A higher frame rate and increased ultrasound transmission events can guarantee excellent ultrasound images. However, the frame rate is inversely proportional to the number of ultrasound transmission events. Therefore, the ultrasound image must be prevented from degrading, even if the number of ultrasound transmittance events is decreased.

In order to increase the frame rate under the same number of ultrasound transmission events, there exists a method of forming multiple receiving scan lines from one original receiving scan line. In this method, ultrasound outputted from the probe is focused on one transmittance scan line, wherein multiple receiving scan lines are simultaneously formed with ultrasound echoes from the scan line. That is, the multiple scan lines are formed with the ultrasound echoes generated by one transmission event.

In a conventional ultrasound diagnostic system, digital receiving signals are formed by converting the analog receiving signals at a constant extraction rate. Further, a receiving scan line is formed with the digital receiving signals. A time divisional method is used to form multiple scan lines at one time, and all the multiple scan lines should be configured within the same time allowed for single scan line. For an example, one scan line of triple scan lines should be configured within ⅓ time allowed for the single scan line, and therefore the amount of the data is limited in proportional to the allowed time.

If the conventional diagnostic system is designed to extract data at 60 MHz for configuring the single scan line, as the number of receiving scan lines is increased from single to dual, triple or quadruple receiving scan line, the extraction rate per one scan line of the multiple scan lines must be reduced from 60 MHz to 30 MHz, 20 MHz or 15 MHz, respectively. This means that the extraction rate of the single receiving signal is unnecessarily high and the ultrasound diagnostic system should process lots of useless data due to over-sampling. Further, when designing the conventional ultrasound diagnostic system, the change in extraction rates must be considered, which causes an increase in the costs of manufacturing the system.

BRIEF DESCRIPTION OF THE DRAWINGS

Arrangements and embodiments may be described in detail with reference to the following drawings in which like reference numerals refer to like probe elements and wherein.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
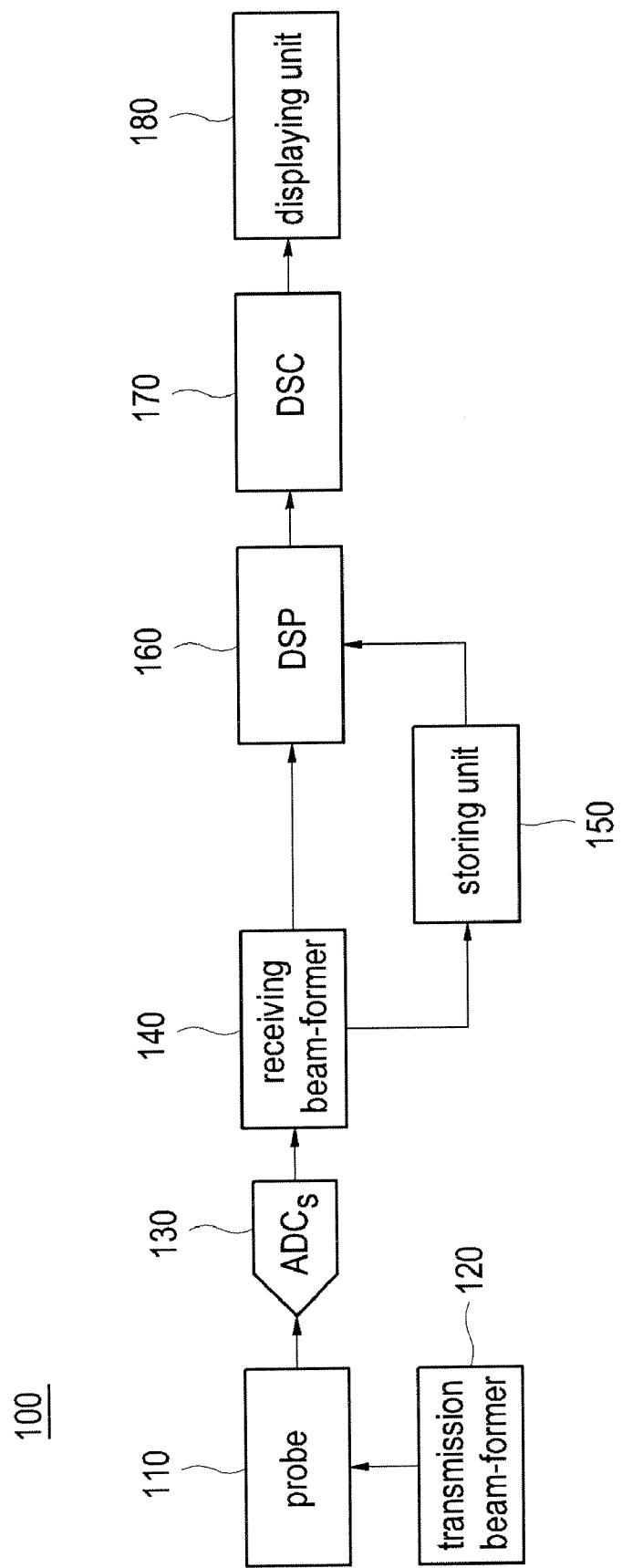
FIG. 1 is a block diagram showing an ultrasound diagnostic system constructed in accordance with the present invention.

FIG. 1 is a block diagram showing an ultrasound diagnostic system constructed in accordance with the present invention. As shown in FIG. 1, the ultrasound diagnostic system 100 includes a probe 110, a transmission beam-former 120, a plurality of analog-digital converters (ADCs) 130, a receiving beam-former 140, a main storing unit 150, a digital signal processor (DSP) 160, a digital scan converter (DSC) 170 and a displaying unit 180.

Figure 2:
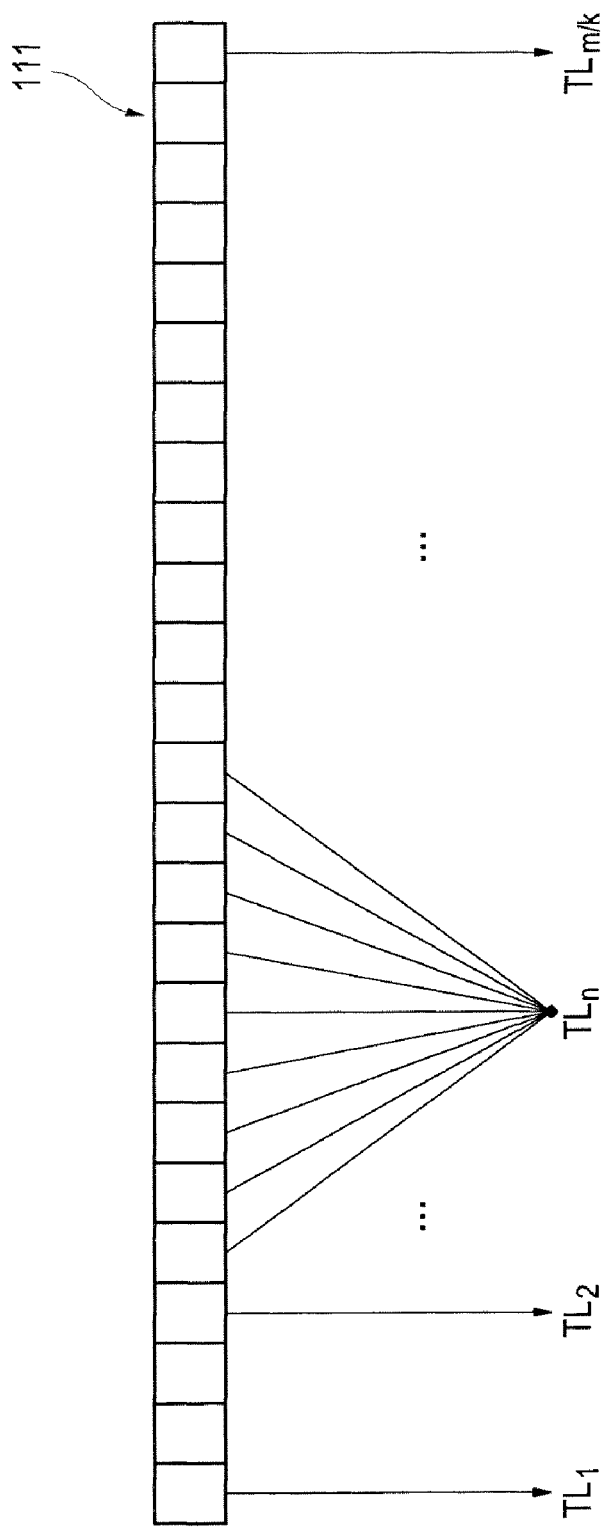
FIG. 2 is a schematic diagram showing a method of focusing an ultrasound transmission signal on a transmission scan line in accordance with the present invention.

The probe 110 includes a plurality of probe elements. Referring to FIG. 2, each probe element 111 converts electrical transmission signals into ultrasound transmission signals and transmits the ultrasound transmission signals to a focal point on a target object along a transmission scan line TLn. The probe element also receives ultrasound echoes from the target object and converts the ultrasound echoes into electrical receive signals of analog-form. The number of probe elements participating in one transmission event and the number of probe elements receiving the ultrasound echoes generated by one event of transmission may depend on the design of the ultrasound diagnostic system 100 or the probe 110. Specifically, the number of probe elements (channels) required to form one original receiving scan line may vary according to the design of the ultrasound diagnostic system 100 or the probe 110. The analog receiving signals outputted from the probe 110 have a center frequency, which reflects the characteristics of the probe 110 and the internal tissues of the target object.

The transmission beam-former 120 forms a transmission beam, which is transmitted from the probe elements 111 to a transmission scan line TLn, as shown in FIG. 2. When forming "m" numbers of receiving scan lines according to the method of forming "k"-multiple scan lines, "m/k" transmission scan lines are required, wherein "m" and "k" are positive integers. For instance, 256/4 transmission scan lines are required to form 256 receiving scan lines with the method of forming 4-multiple (quadruple) scan lines.

Figure 3:
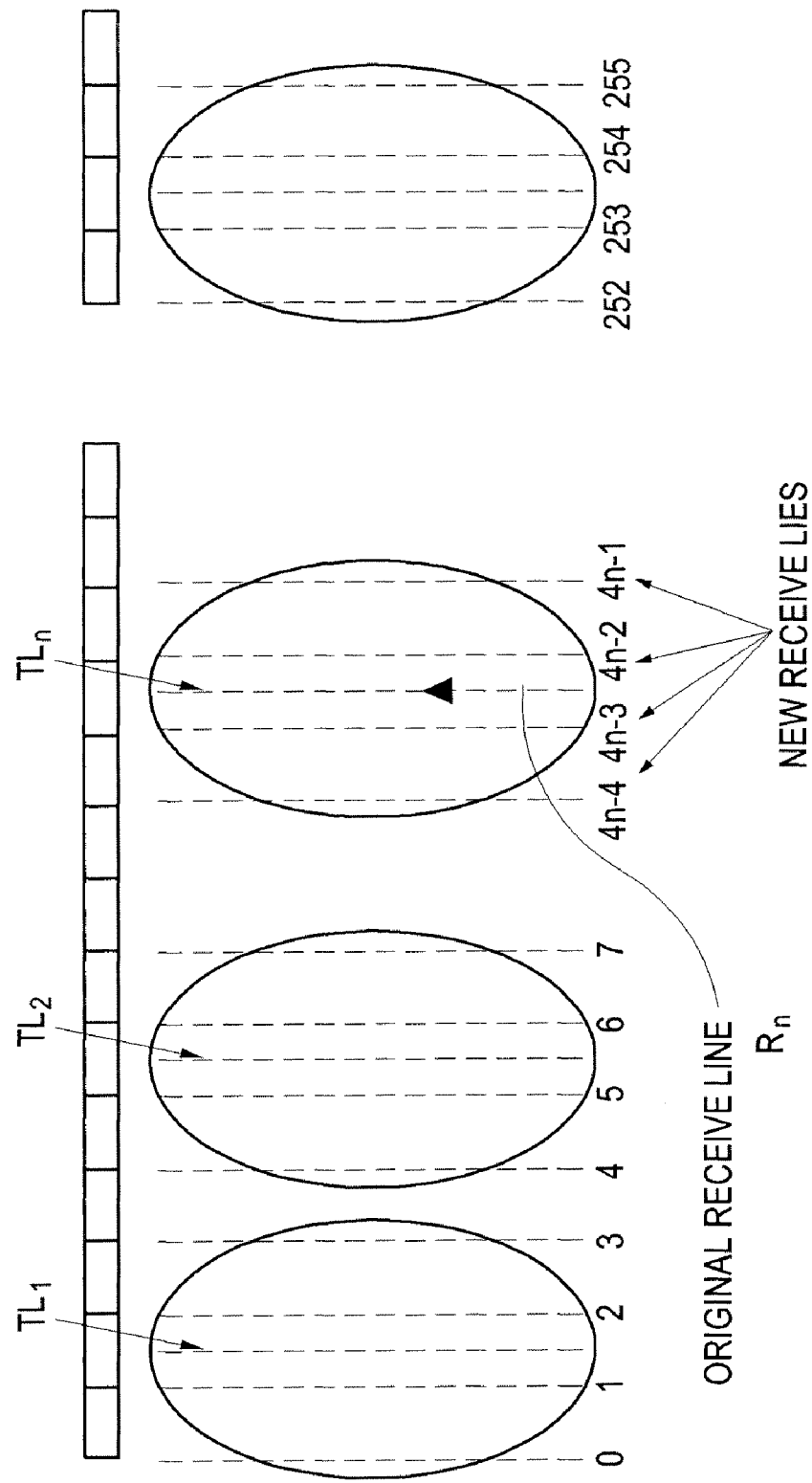
FIG. 3 is a schematic diagram showing a method of forming receiving scan lines in accordance with the present invention.

Referring to FIGS. 2 and 3, the ultrasound signals are transmitted from the probe elements 111 to one of the transmission scan lines $TL_1, TL_2 \ldots TLn$. As shown in FIG. 3, the probe elements 111 receive the ultrasound echoes along one original receiving scan line Rn. Multiple scan lines (e.g., quadruple scan lines 4n-1, 4n-2, 4n-3 and 4n-4) are formed with the one original receiving scan line Rn. The original receiving scan line Rn may be disposed on the transmission scan line Tn.

The ADCs 130 form digital data from the analog receiving signals. The number of ADCs 130 is equal to that of the probe elements contributing to form one original receiving scan line (i.e., participating in the same transmission event). Further, the ADCs 130 correspond one-to-one with the probe elements 111. Each ADC samples the analog receiving signals, which are outputted from each probe element 111, at a predetermined sample rate and converts the analog receiving signals into the digital data. The predetermined sample rate may be 60 MHz.

The receiving beam-former 140 forms the data of multiple scan lines from the digital data outputted from the ADC 130. Specifically, the receiving beam-former 140 delays the digital data, extracts the delayed digital data at a rate of n-times of the center frequency of the analog receiving signals, and performs an interpolation with the extracted digital data to form the data of multiple receiving scan lines.

The data of multiple receiving scan lines are temporarily stored in the main storing unit 150. The main storing unit 150 may be configured with a register. The DSP 160 forms the image data to display the target object in B, C or D mode by processing the data inputted from the receiving beam-former 140 or the main storing unit 150. The DSC 170 scan-converts a scan-conversion to the image data. Further, the displaying unit 180 displays an ultrasound image with the scan-converted image data.

Figure 4:
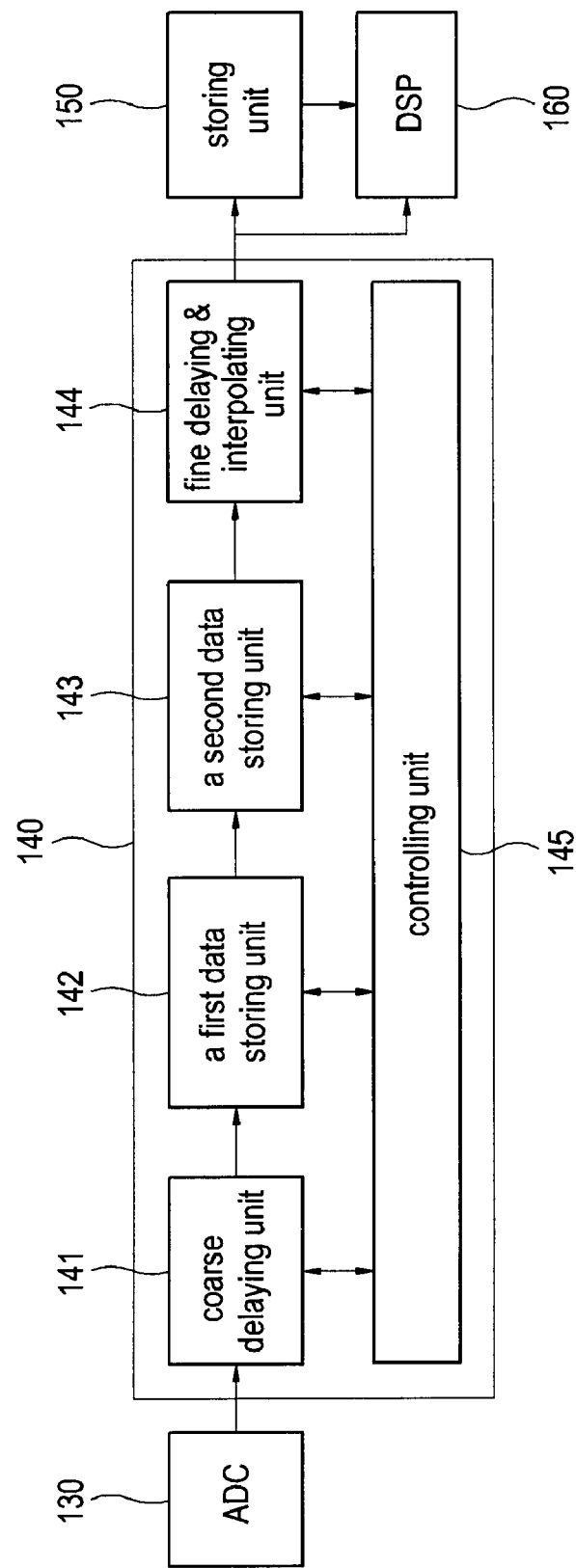
FIG. 4 is a block diagram showing a receiving beam-former constructed in accordance with the present invention.

The receiving beam-former 140 is described below in detail. Referring to FIG. 4, the receiving beam-former 140 includes coarse delaying units 141, first data storing units 142, second data storing units 143, a fine delaying and interpolating unit 144 and a controlling unit 145.

Figure 5:
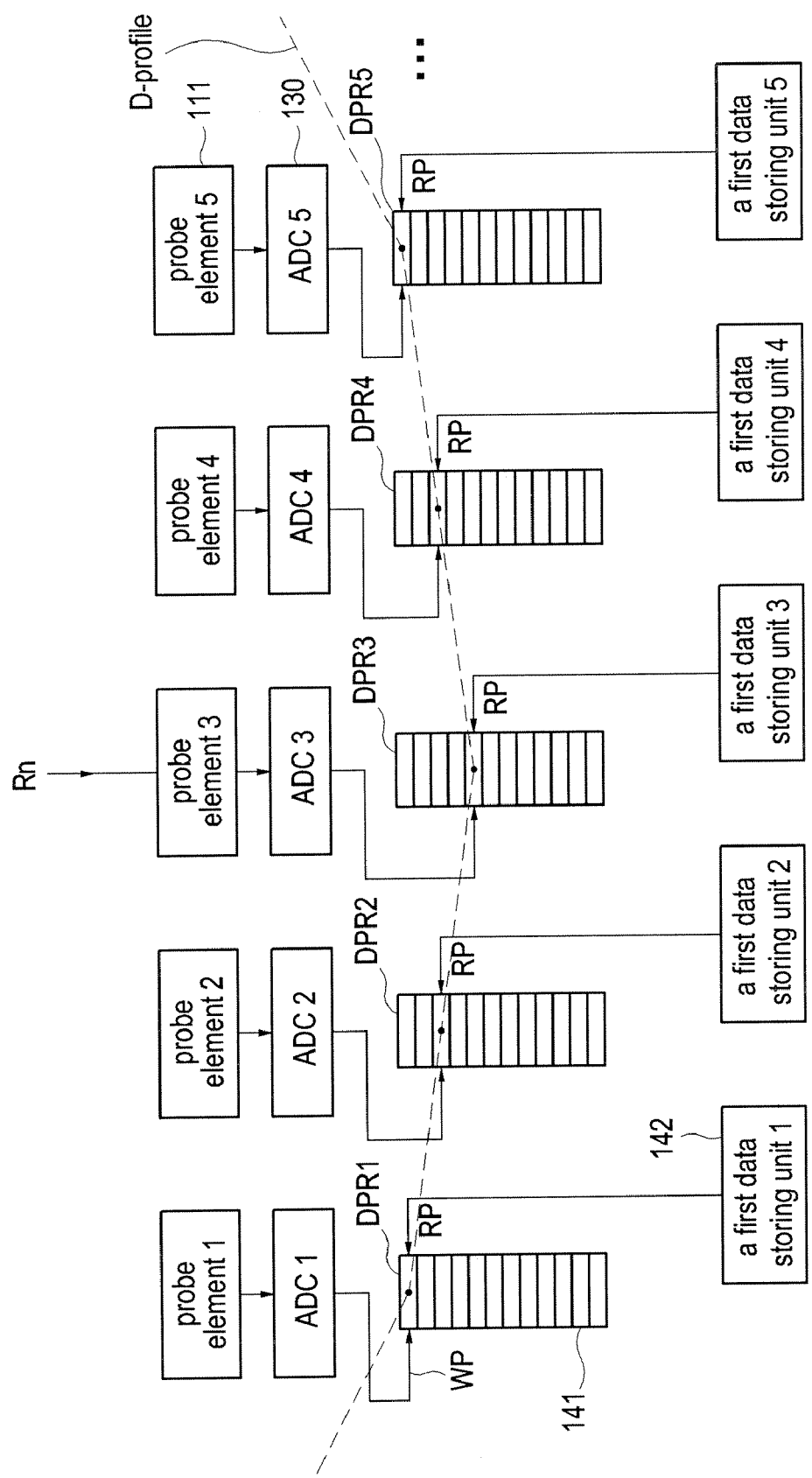
FIG. 5 is a schematic diagram showing the relations between probe elements, analog-digital converters, coarse delay units and first data storing units constructed in accordance with the present invention.

The coarse delaying unit 141 may be configured with a plurality of dual-port random access memories (RAMs). The number of dual-port RAMs may be equal to the number of ADCs 130. Further, the dual-port RAMs correspond one-to-one with the ADCs 130, as shown in FIG. 5. The dual-port RAM includes a plurality of storing regions, a writing pointer WP, a reading pointer RP, a writing pin (not shown) and a reading pin (not shown). The data inputted through the writing pin are stored in the storing region pointed by the writing pointer WP. Also, the data stored in a storing region pointed by the reading pointer RP are outputted through the reading pin. All the writing and the reading pointers of the DPRs indicate the same storing region at an initial state when the digital data obtained from one transmission event has not been outputted from any of the ADCs 130. They begin to move among the storing regions at the same speed as the digital data are inputted. The reading pointer of each DPR is controlled in consideration of the distance differences between a specific point on the original receiving scan line Rn and the probe elements 111.

The digital data outputted from ADCs 130 are stored in the storing regions of the corresponding DPR one after another. For example, if five probe elements receive the ultrasound echoes generated by one event of the transmission, then the digital data outputted from each ADC and ADC1 to ADC5 are stored in each DPR and DPR1 to DPR5 at different times according to the delay profile (D-profile), as shown in FIG. 5. In another configuration, at a predetermined time from storing data in each region or from pointing each region with the writing pointer, the reading pointer may point the region under the control of the controlling unit 145. Therefore, the coarse delay unit 141 may output coarsely delayed data under the control of the controlling unit 145. To reduce the size of the coarse delaying unit 141 and to lower costs, the coarse delaying unit 141 may be configured with single DPR instead of the plurality of DPRs. In such a case, the digital data from each ADC are stored in different storing regions of the single DRP.

The first data storing units 142 store the coarsely delayed data outputted from the coarse delaying unit 141. The number of first data storing unit is also equal to that of the probe elements contributing to form one receiving scan line. Each first data storing unit 142 has a plurality of storing regions. Preferably, the first data storing unit 142 may be configured with the shift registers.

The second data storing units 143 store data extracted from the first storing unit 142 at a rate of n-times of the center frequency, wherein "n" denotes a positive integer. The second data storing unit 143 may be configured with a processing resister, which also provides a plurality of storing regions. The number of second data storing unit is also equal to that of the probe elements contributing to form one receiving scan line. Further, the second data storing units 143 correspond one-to-one with the first data storing unit 142.

Information of the center frequency may be directly provided by a user such as a system designer or an operator. The ultrasound diagnostic system may further include a center frequency providing unit, which analyzes the analog receiving signals outputted from the probe elements and provides the information of the center frequency as a result of the analysis.

The controlling unit 145 extracts the delayed digital data from the first data storing unit 142 at a rate DR, which is defined as the following equation 1.

$$DR = n \times fc \quad (1)$$

In equation 1, "n" and "fc" denote a positive integer and the center frequency of the analog signals, respectively. For example, if the center frequency $f_c$ is 5 MHz and n is 4, then the controlling unit 145 extracts the data stored in the first data storing unit 142 at a rate of 4-times of the center frequency, i.e., 4×5=20 MHz, regardless of the number of receiving scan lines. As a further example, if the center frequency $f_c$ is 2.5 MHz, then the controlling unit 145 extracts the data stored in the first data storing unit 142 at a rate of 4-times of the center frequency, i.e., at the rate of 4×2.5=10 MHz, regardless of the number of receiving scan lines.

The controlling unit 145 also selects parts of the data in the second data storing unit 143 n-times of the center frequency in order to obtain interpolation data. The controlling unit 145 selects the data repeatedly as many as the number of multiple receiving scan lines formed with one original receiving scan line. The controlling unit 145 selects the data stored in the second data storing unit 143 at a rate CR, which is defined as the following equation 2.

$$CR = k \times n \times fc \qquad (2)$$

In equation 2, "k" denotes the number of receiving scan lines to be obtained with one original receiving scan line, "n" denotes a positive integer and "fc" denotes the center frequency of the analog signals. For example, if the center frequency $f_c$ is 5 MHz and it is designed to form triple receiving scan lines from one original receiving scan line, then the controlling unit 145 selects the data at a rate of 4-times of the center frequency and the number of multiple receiving scan lines at the rate of 3×4×5=60 MHz. Thus, the data selection for one receiving scan line of the triple scan lines performed at the rate of 60÷3=20 MHz(=CR/k). As another example, if the center frequency $f_c$ is 2.5 MHz and it is designed to form sextuple receiving scan lines with one original receiving scan line, then the controlling unit 145 selects the data at a rate of 4-times of the center frequency and the number of multiple receiving scan lines at the rate of 6×4×2.5=60 MHz. At this time, the data selection for one receiving scan line is performed at the rate of 60÷6=10 MHz(=CR/k). Accordingly, the data selection for obtaining interpolation data can be selected at a constant rate, regardless of the number of receiving scan lines.

Figure 6:
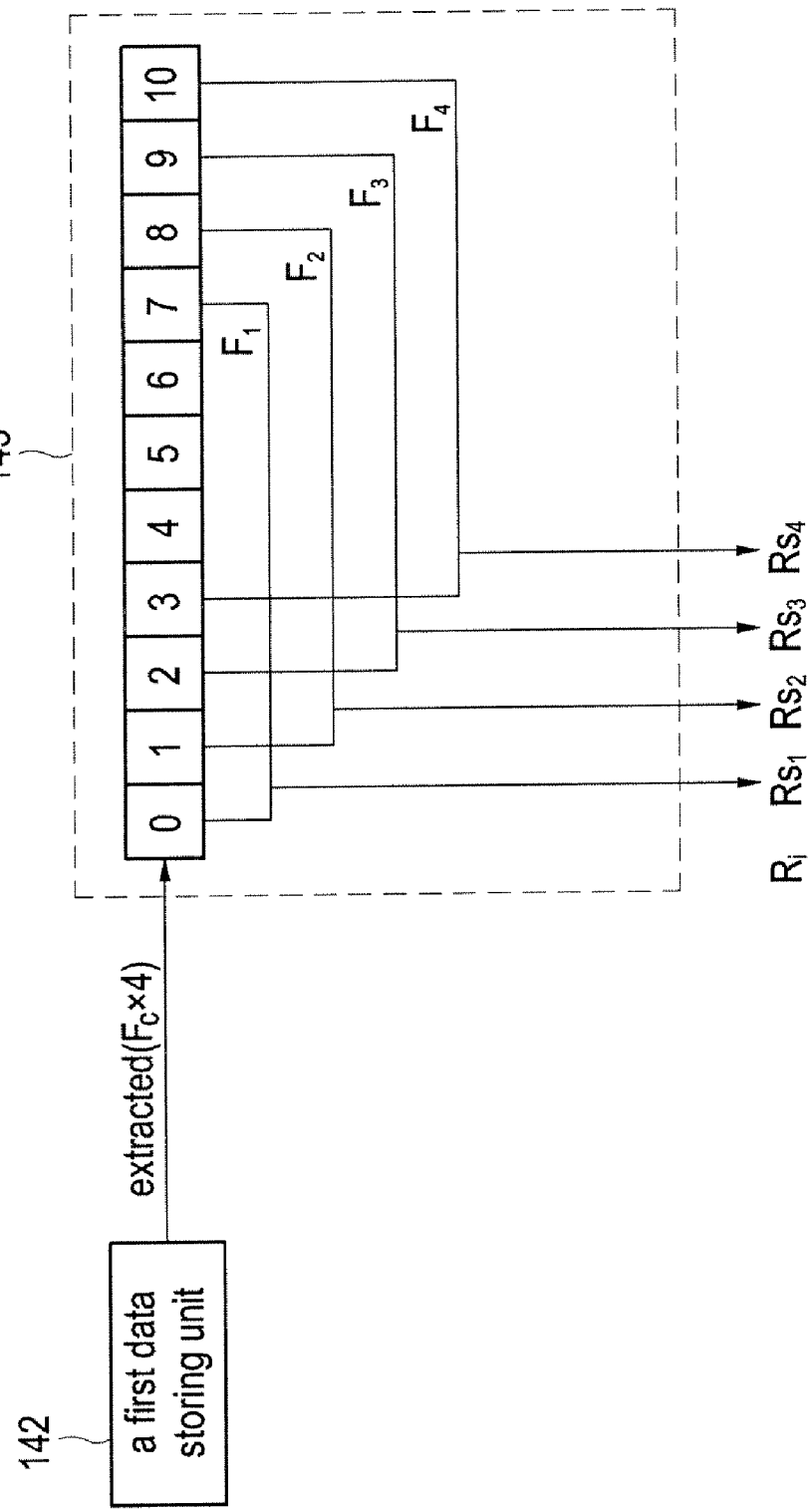
FIG. 6 is a schematic diagram illustrating the extraction and selection of data in accordance with the present invention.

The number of selected data is equal to that of the receiving scan line to be formed with one original receiving scan line. Referring to FIG. 6, the controlling 145 selects the data by moving a filter window four times to form quadruple receiving scan lines from one original receiving scan line. The filter window may have an 8-point size. In FIG. 6, "F1", "F2", "F3" and "F4" denote the movement of filter window, whereas "RSi" denotes an output of i-th movement of the filter, i.e., "$RS_1$", "$RS_2$", "$RS_3$" and "$RS_4$" denote outputs of first, second, third and fourth movements of the filter, respectively.

Figure 7:
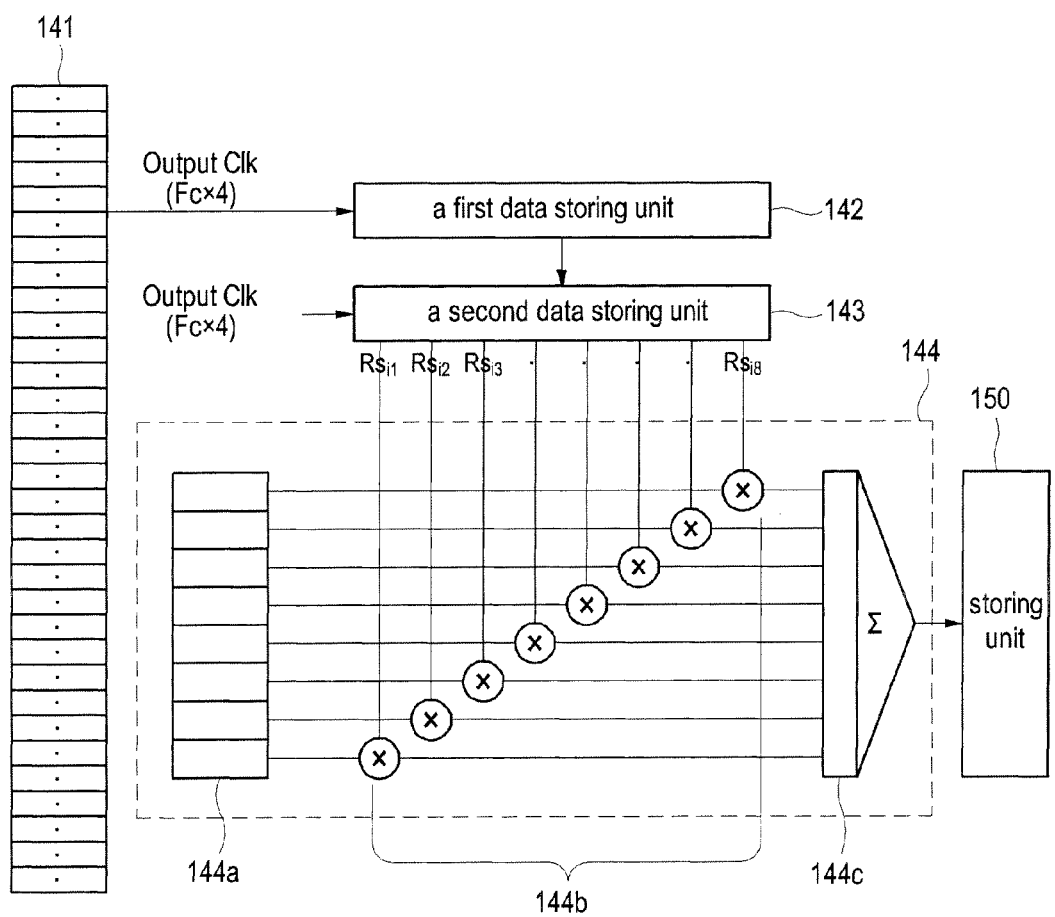
FIG. 7 is a schematic diagram showing a coarse delaying unit, first and second extracted data storing units and a fine delaying and interpolating unit constructed in accordance with the present invention.

The fine delaying and interpolating unit 144 performs a fine delay and interpolates the data of each receiving scan line, which is selected from the second data storing unit 143 at the rate of n-times of the center frequency and the multiple receiving scan lines under the control of the controlling unit 145. As shown in FIG. 7 the fine delaying and interpolating unit 144 includes a coefficient RAM 144a, a plurality of multipliers 144b and an adder 144c. The coefficient RAM 144a provides a look-up table of interpolation filter coefficients for the fine delay and the interpolation. The multipliers 144b correspond one-to-one with selected data and interpolation coefficient filters and multiply the filter coefficients to the selected data. The adder 144c adds the outputs of the multipliers 144b to form the interpolated data, which are to be used to form one receiving scan line among the multiple receiving scan lines. By interpolating the data extracted and selected at the rate of n-times of the center frequency, a finely delayed data can be obtained.

Although a gain controlling unit, which is used to form the receiving beam, is omitted in FIG. 4, it is natural that the receiving beam-former 140 includes the gain controlling unit to perform the basic function thereof.

As mentioned above, the data is extracted and selected at the rate of n-time of the center frequency in order to form the multiple receiving scan lines from one original receiving scan line. Therefore, lowering the extraction rate and the selection rate can be prevented, even though the number of receiving scan lines is increased.

An ultrasound diagnostic system for forming multiple receiving scan lines with one original receiving scan line is disclosed. This system includes: a plurality of probe elements for changing ultrasound echoes from one original receiving scan line into analog signals, wherein the analog signals have a center frequency; an analog-digital converter for converting the analog signals into digital data; and a receiving beam-former for coarsely delaying the digital data, storing the coarsely delayed data, extracting the coarsely delayed data at a rate of n-times of the center frequency, and forming data of multiple scan lines by performing a fine delay and interpolation with the extracted data, wherein n is a natural number.

Also, there is provided a method of forming multiple receiving scan lines with one original receiving scan line. This method includes: changing ultrasound signals reflected from one original receiving scan line into analog signals, wherein the analog signals have a center frequency; converting the analog signals into digital data; coarsely delaying the digital data; storing the coarsely delayed data; extracting the coarsely delayed data at a rate of n-times of the center frequency, wherein n is a natural number; and forming multiple scan lines with the extracted data.

Any reference in this specification to "one embodiment," "an embodiment," "example embodiment," etc., means that a particular feature, structure or characteristic described in connection with the embodiment is included in at least one embodiment of the invention. The appearances of such phrases in various places in the specification are not necessarily all referring to the same embodiment. Further, when a particular feature, structure or characteristic is described in connection with any embodiment, it is submitted that it is within the purview of one skilled in the art to effect such feature, structure or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound diagnostic system for forming multiple receiving scan lines with one original receiving scan line, comprising:

a plurality of probe elements configured to change ultrasound echoes from one original receiving scan line into analog signals, wherein the analog signals have a center frequency;

an analog-digital converter configured to convert the analog signals into digital data; and a receiving beam-former configured to form data of the multiple receiving scan lines based on the digital data, wherein the receiving beam-former includes, coarse delaying units configured to coarsely delay the digital data from analog-digital converter, first storing units configured to store the coarsely delayed data, a controlling unit configured to extract the data stored in the first storing units at a rate defined by $$DR = n \times fc,$$

second storing units configured to store data extracted from the first storing units, wherein the controlling unit is further configured to select the data stored in the second storing units repeatedly, as many as a number of the multiple receiving scan lines at a rate defined by $$CR = k \times n \times fc,$$ and a fine delaying and interpolating unit configured to perform fine delay and interpolation to the selected data to form data of the multiple receiving scan lines, wherein "DR" and "CR" denote an extraction rate and a selection rate, respectively, and "n," "fc" and "k" denote a positive integer, the center frequency and the number of the multiple receiving scan lines, respectively, which are provided by a user during an operation of the system.

2. The system of claim 1, wherein the controlling unit is further configured to control the coarse delaying unit, the first and second delaying units, and the fine delaying and interpolating unit.

3. The system of claim 2, wherein a number of the coarse delaying units, the first and second storing units are equal to a number of the plurality of probe elements contributing to form the one original receiving scan line, and the coarse delaying units, and wherein the first and second storing units correspond one-to-one with the probe elements.

4. The system of claim 2, wherein the controlling unit selects the data by moving a filter having a predetermined size repeatedly as many as the number of the multiple receiving scan lines.

5. The system of claim 2, wherein the fine delaying and interpolating unit includes:
a coefficient RAM configured to provide a look-up table of filter coefficients for the fine delay and the interpolation;
a plurality of multipliers configured to multiply the filter coefficients to the selected data; and
an adder configured to add outputs of the multipliers.

6. The system of claim 5, further comprising:
a main storing unit configured to store the data of the multiple receiving scan lines;
a scan converting unit configured to scan-convert the data of the multiple receiving scan lines; and
a displaying unit configured to display ultrasound images with the scan-converted data.

7. A method of forming multiple receiving scan lines with one original receiving scan line, comprising:
changing ultrasound signals reflected from one original receiving scan line into analog signals, wherein the analog signals have a center frequency;
converting the analog signals into digital data using an analog-digital converter;
coarsely delaying the digital data;
storing the coarsely delayed data;
extracting the coarsely delayed data at a rate defined by $$DR = n \times fc,$$

storing the extracted data;
selecting a part of the data, repeatedly, as many as a number of the multiple receiving scan lines at the rate defined by $$CR = k \times n \times fc,$$ and performing fine delay and interpolation to the selected data to form the data of the multiple receiving scan lines, wherein "DR" and "CR" denote an extraction rate and a selection rate, respectively, and "n," "fc" and "k" denote a positive integer, the center frequency and the number of the multiple receiving scan lines, respectively, which are provided by a user when executing the method.

8. The method of claim 7, wherein a part of the extracted data is selected by moving a filter having a predetermined size repeatedly as many as the number of the multiple receiving scan lines.

* * * * *